US00PP37542P3

(12) United States Plant Patent
Rietberg

(10) Patent No.: US PP37,542 P3
(45) Date of Patent: Jul. 28, 2026

(54) ***HEBE* PLANT NAMED 'Maya'**

(50) Latin Name: ***Hebe* hybrid**
Varietal Denomination: Maya

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 19/384,961

(22) Filed: Nov. 10, 2025

(65) Prior Publication Data

US 2026/0144175 P1 May 21, 2026

(30) Foreign Application Priority Data

Nov. 19, 2024 (QZ) ..... PBR 20242674

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hebe* plant named 'Maya' that is characterized by its consistently healthy plants with a low susceptibility to foliage diseases, its compact plant habit, its floriferous blooming habit and a long blooming period, its flowers that are bright violet in color, its self-cleaning flowers, and its bright green colored foliage.

3 Drawing Sheets

Botanical classification: *Hebe* hybrid.
Cultivar designation: 'Maya'.

CROSS REFERENCE TO A RELATED APPLICATION

This application claims priority to European Community Plant Variety Office (CPVO) Plant Breeder's Rights Application No. 2024/2674 filed on Nov. 19, 2024, under 35 U.S.C. 119(f), the entire contents of which is incorporated by reference herein. The information for the Plant Breeders' Rights was received directly from the Inventor.

BACKGROUND OF THE INVENTION

The present invention relates to a new and distinct cultivar of *Hebe*, botanically of hybrid origin, known as *Hebe* 'Maya', and will be referred to hereafter by its cultivar name, 'Maya'. 'Maya' is an evergreen shrub grown for use as a container plant and as a landscape shrub.

The new cultivar was derived from a controlled breeding program conducted by the Inventor in Wezep, The Netherlands. The goals of the breeding program are to select new cultivars of *Hebe* with good plant health, compact and globular plant habits, abundant flowering, vibrant flower colors, and self-cleaning flowers. The new cultivar arose from a cross made in September of 2021 between unnamed and unpatented proprietary plants from the Inventor's breeding program; reference no. HS20-2006 as the female parent and ref no. PM20-5000 as the male parent. The Inventor selected 'Maya' in September of 2022 as a single unique plant amongst the seedlings that resulted from the above cross.

Asexual propagation of the new cultivar was first accomplished by stem cuttings in October of 2022 by the Inventor in Wezep, The Netherlands. Asexual propagation by stem cuttings has determined the characteristics of the new cultivar are stable and reproduced true to type in successive generations.

SUMMARY OF THE INVENTION

The following traits have been repeatedly observed and represent the characteristics of the new cultivar, which in combination distinguish 'Maya' as a new and distinct cultivar of *Hebe*.

1. 'Maya' exhibits consistently healthy plants with a low susceptibility to foliage diseases.
2. 'Maya' exhibits a compact plant habit.
3. 'Maya' exhibits a floriferous blooming habit and a long blooming period.
4. 'Maya' exhibits flowers that are bright violet in color.
5. 'Maya' exhibits self-cleaning flowers.
6. 'Maya' exhibits bright green colored foliage.

The female parent of 'Maya' differs from 'Maya' in having flowers that are less intense in color and a less vigorous growth habit. The male parent of 'Maya' differs from 'Maya' in having leaves that are darker green in color, flowers that are white in color, and a less vigorous growth habit. 'Maya' can be most closely compared to the *Hebe* cultivars 'HM150203' (U.S. Plant Pat. No. 34,920) and 'Blue Mist' (not patented). 'HM150203' is similar to 'Maya' in inflorescence shape. 'HM150203' differs from 'Maya' in having a more compact plant habit, a smaller plant size, a less floriferous blooming habit, and foliage that is lighter green in color. 'Blue Mist' is similar to 'Maya' in flower color. 'Blue Mist' differs from 'Maya' in having a less compact plant habit, larger sized flowers, a less floriferous blooming habit, and foliage that is darker green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium, Facebook, Instagram, and Groen-Direkt Boskoop.

BRIEF DESCRIPTION OF THE DRAWINGS

The accompanying color photographs illustrate the overall appearance and distinct characteristics of the new *Hebe*. The photographs were taken of a 7-month-old plant of 'Maya' as grown outdoors in a 10.5-cm container in Wezep, The Netherlands.

The photograph in FIG. 1 provides a side view of a plant of 'Maya' in bloom.

Figure 1:
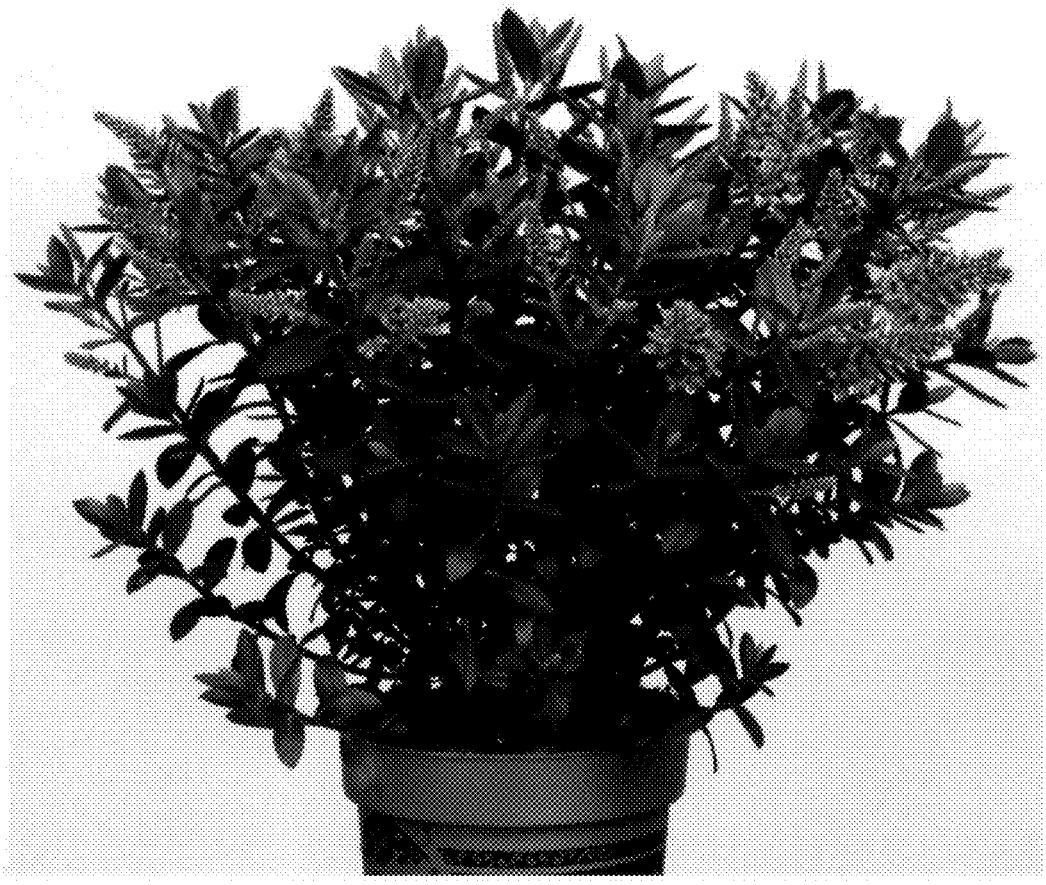
Figure 2:
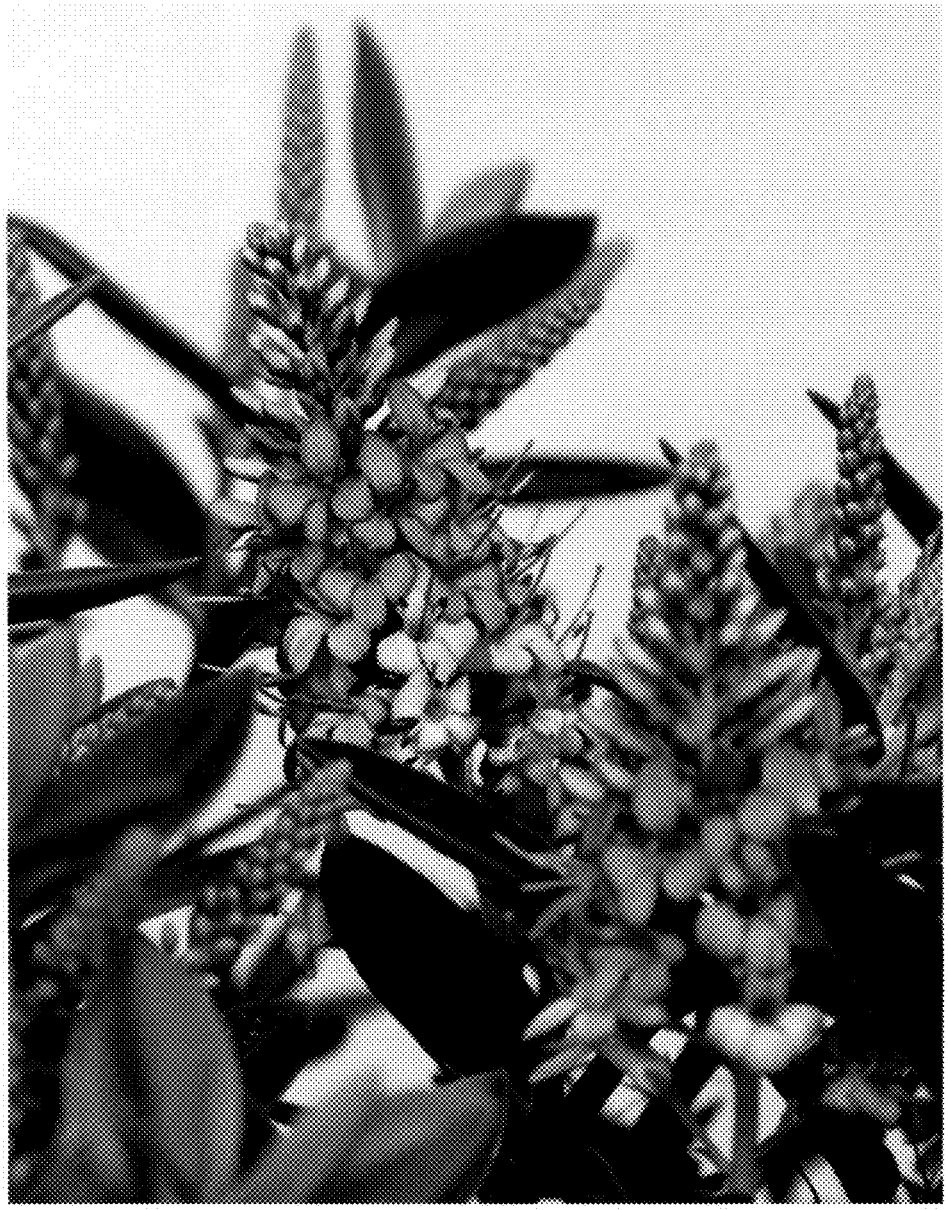

The photograph in FIG. 2 provides a close-up of the inflorescences of 'Maya'.

Figure 3:
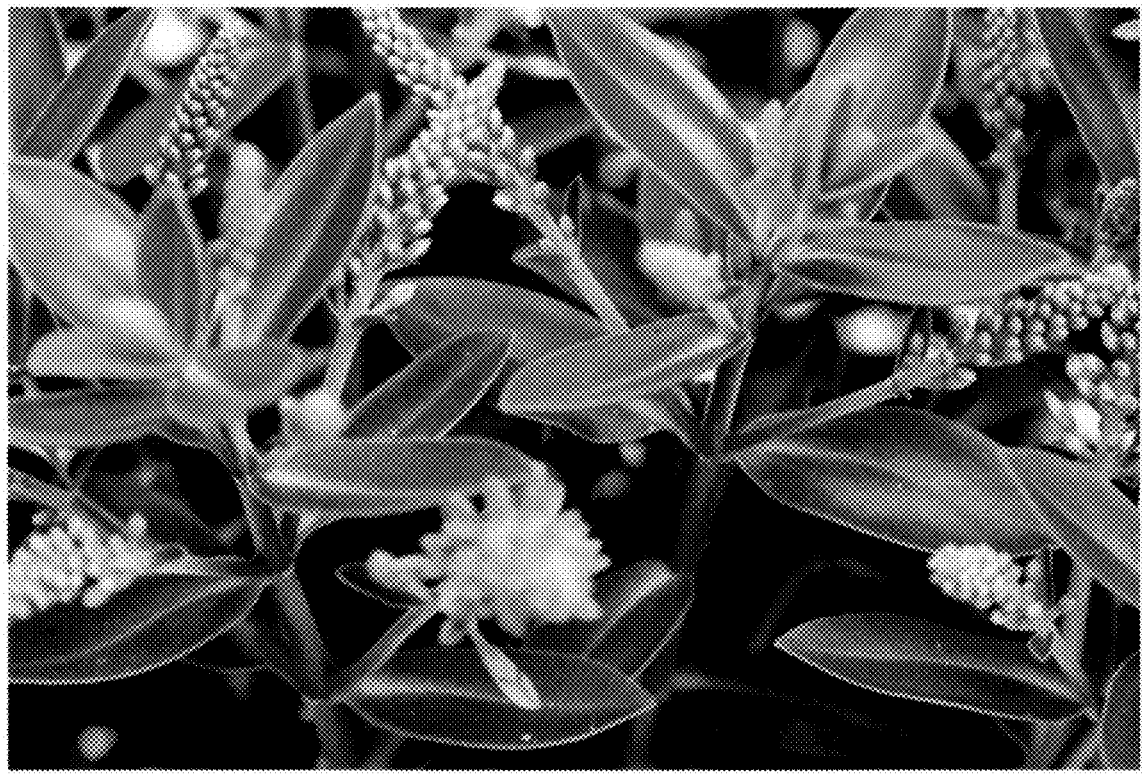

The photograph in FIG. 3 provides a close-up view of the foliage of 'Maya'.

The colors in the photograph may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 10.5-cm containers in Wezep, The Netherlands. The phenotype of the new cultivar may vary with variations in environmental, climatic, and cultural conditions, as it has not been tested under all possible environmental conditions. The color determination is in accordance with the 6$^{th}$ edition 2019 (reprint of 2015 edition) Colour Chart of The Royal Horticultural Society, London, England, except where general color terms of ordinary dictionary significance are used.

General description:

*Blooming period*.—Summer into fall in The Netherlands.

*Plant type*.—Evergreen shrub.

*Plant habit*.—Compact.

*Height and spread*.—Reaches an average of 20 cm in height and 30 cm spread as a one-year-old plant as grown in the landscape.

*Cold hardiness*.—At least to U.S.D.A. Zone 8.

*Diseases and pests*.—Observed to have low susceptibility to leaf spot disease (*Septoria veronicae*) and downy mildew (*Perenospora* ssp.), no susceptibility or resistance to pests has been observed.

*Root description*.—Fibrous to slightly fleshy.

*Propagation*.—Softwood stem cuttings.

*Root development*.—Root initiation occurs in 3 weeks in summer and 6 weeks in winter, a fully rooted cutting is produced in about 2 months.

*Growth rate*.—Moderate.

Branch description:

*Branch size*.—Average of 17.7 cm in length and 2.5 mm in diameter.

*Branch shape*.—Round.

*Branch color*.—Young; 187B, mature; 176B, lower side 145A, internodes 178A, bark; 146A.

*Branch surface*.—Surface luster is slightly glossy, densely covered with very short glandular hairs; 0.1 mm in length, matches surface color.

*Branch strength*.—Strong.

*Branch aspect*.—Held in an average angle of 45°.

*Internode length*.—Average of 1.5 cm.

*Branching habit*.—8 main branches, 7 lateral branches per main branch.

Foliage description:

*Leaf shape*.—Elliptic, slightly carinate.

*Leaf division*.—Single.

*Leaf base*.—Attenuate.

*Leaf apex*.—Acute.

*Leaf venation*.—Pinnate, color upper surface; 147C, color lower surface; 146D.

*Leaf margins*.—Entire, moderately covered with short glandular hairs.

*Leaf attachment*.—Petiolate.

*Leaf arrangement*.—Opposite.

*Leaf surface*.—Both surfaces smooth, glabrous, non-rugose, upper surface moderately glossy, lower surface slightly glossy.

*Leaf color*.—Young upper surface; 137A, young lower surface; 138A, mature upper surface; NN137A, mature lower surface; 146B.

*Leaf size*.—An average of 2.9 cm in length and 1.3 cm in width.

*Petioles*.—1 mm in length, 1 mm in diameter, flattened, both surfaces are smooth, glabrous, and very slightly glossy, margins moderately covered with short glandular hairs, strong, color; upper surface 147C, margins 183C, lower surface 144D, margins 183A.

Flower description:

*Inflorescence type*.—Raceme.

*Inflorescence size*.—Average of 4.7 cm in height and 2.8 cm in width.

*Inflorescence lastingness*.—About 7 days, self-cleaning flowers.

*Flower shape*.—Campanulate.

*Flower fragrance*.—None.

*Flower quantity*.—Average 60 flowers per inflorescence, 800 flowers per plant, 4,200flowers and flower buds per plant.

*Flower arrangement*.—Axillary racemes.

*Flower aspect*.—Outward.

*Flower size*.—Average of 1.1 cm in height and depth, 8 mm in diameter, throat 1 mm in diameter, flower tube 3 mm in length and 2 mm in diameter.

*Peduncles*.—Strong strength, 6.4 cm in length and about 1 mm in diameter, 144B to 144C in color, held at about a 45° angle to vertical, surface is very slightly glossy and densely covered with very short glandular hairs; an average of 0.1 mm in length, color matches surface color.

*Pedicels*.—Moderately strong, surface is matte, average of 2 mm in length and 0.5 mm in diameter, held in a 45° angle to peduncle, 144B in color.

*Flower buds*.—Narrow elliptic, 5 mm in length and 1.75 mm in diameter, narrow elliptic in shape, surface is matte, smooth and glabrous, color; N88C, immature calyx 138B.

*Petals*.—Average 4, 1 whorl, 37.5% of base is fused, moderately reflexed, upper petal elliptic, lateral lower petals broadly ovate, dorsal lower petal ovate, size; all petals 5 mm in length, of upper and lower lateral petals; 3 mm in width, dorsal lower petal 2 mm in width, all petals; entire margins, apex obtuse, surface upper and lower surface; smooth, glabrous, non-rugose, and matte, color; when opening upper surface N87B, when opening lower surface N87D, margins N87B, when fully open upper surface N87C, when fully open lower surface N87D, margins N87C, upper surface fading to a blend of N87D and N88D, lower surface fading to 85A, throat color 85C, tube inner and outer surface 85C, base 155C.

*Calyx*.—Rotate-shaped, average of 2.5 mm in length and 2 mm in diameter.

*Sepals*.—4, 2 upper, 2 lower, ovate in shape with entire margins, 2.5 mm in length, 1 mm in length, rotate, bluntly acute apex, base cuneate and 40% fused, both surfaces glabrous, upper surface slightly glossy, lower surface slightly matte, color; when opening and fully open upper and lower surface 138B.

*Floral bracts*.—A single bract is placed below each individual flower, narrow ovate in shape, acute apex, cuneate base, 2 mm in length, 0.75 mm in width, both surfaces glabrous and 138A in color.

Reproductive organs:

*Gynoecium*.—Pistil; 1, 9.5 mm in length, stigma; 0.5 mm in diameter, club-shaped, 76D in color, style; 9 mm in length, N75A in color, ovary; 146A in color.

*Androecium*.—Stamens; 2, anthers; oblong in shape, 1.5 mm in length, 0.5 mm in width and 152B in color, filaments; 7 mm in length, N87D in color, pollen; none observed.

*Fruit and seed*.—None observed to date.

It is claimed:

1. A new and distinct cultivar of *Hebe* plant named 'Maya' as herein illustrated and described.

* * * * *